(12) United States Patent
Baxter et al.

(10) Patent No.: US 9,616,204 B2
(45) Date of Patent: Apr. 11, 2017

(54) DILATION CAP FOR ENDOLUMINAL DEVICE

(71) Applicant: Cook Medical Technologies LLC, Bloomington, IN (US)

(72) Inventors: Charles Baxter, Greenwood, IN (US); Zachary Wagner, Lafayette, IN (US)

(73) Assignee: Cook Medical Technologies LLC., Bloomington, IN (US)

( * ) Notice: Subject to any disclaimer, the term of this patent is extended or adjusted under 35 U.S.C. 154(b) by 777 days.

(21) Appl. No.: 13/777,170

(22) Filed: Feb. 26, 2013

(65) Prior Publication Data

US 2013/0231634 A1 Sep. 5, 2013

Related U.S. Application Data

(60) Provisional application No. 61/605,934, filed on Mar. 2, 2012.

(51) Int. Cl.
*A61M 29/00* (2006.01)
*A61B 17/34* (2006.01)
(Continued)

(52) U.S. Cl.
CPC ......... *A61M 29/00* (2013.01); *A61B 17/0218* (2013.01); *A61B 17/3478* (2013.01);
(Continued)

(58) Field of Classification Search
CPC .......... A61M 25/0067; A61M 25/0068; A61M 25/0069; A61M 25/007; A61M 25/0082;
(Continued)

(56) References Cited

U.S. PATENT DOCUMENTS 291,364 A * 1/1884 Laskey ............... A61M 3/0279
604/275
835,496 A * 11/1906 Brandon ............. A61M 3/0283
604/103
(Continued)

FOREIGN PATENT DOCUMENTS

JP 2002-306606 A 10/2002
WO WO94/28953 A1 12/1994
(Continued)

OTHER PUBLICATIONS

Extended European Search Report, dated Jun. 19, 2013, European Patent Application No. 13156595.4, European Patent Office, Berlin, Germany, pp. 1-5.
(Continued)

*Primary Examiner* — Imani Hayman
*Assistant Examiner* — Laura Schell
(74) *Attorney, Agent, or Firm* — Brinks Gilson & Lione (57) ABSTRACT

A dilation cap may include a distal tip, an intermediate body, and a proximal coupling member. The distal tip may at least partially surround a longitudinal axis of the dilation cap and may include a cavity to receive a distal end of a cannula of a medical device. The intermediate body may extend proximally from the distal tip and include a dilator portion. The dilator portion may include a projection extending laterally in a direction away from the longitudinal axis of the dilation cap. The proximal coupling member may extend proximally from the intermediate body and at least partially surround the longitudinal axis of the dilation cap. The proximal coupling member may be configured to engage an intermediate portion of the cannula of the medical device. The intermediate body may be asymmetrical with respect to the longitudinal axis of the dilation cap.

11 Claims, 7 Drawing Sheets

(51) Int. Cl.
*A61M 25/00* (2006.01)
*A61B 17/02* (2006.01)
*A61B 17/00* (2006.01)

(52) U.S. Cl.
CPC .... *A61M 25/0069* (2013.01); *A61M 25/0084* (2013.01); *A61B 2017/00805* (2013.01); *A61B 2017/00893* (2013.01); *A61B 2017/3456* (2013.01); *A61M 2025/0087* (2013.01)

(58) Field of Classification Search
CPC ...... A61M 25/0084; A61M 2025/0087; A61M 2025/0092; A61M 29/00; A61M 3/0291; A61M 1/008; A61M 2025/0073; A61M 2025/0095; A61M 2025/0096; A61M 3/0279–3/06; A61B 2017/320044; A61B 17/3478; A61B 2017/00805
See application file for complete search history.

(56) References Cited

U.S. PATENT DOCUMENTS

| | | | |
|---|---|---|---|
| 1,050,803 A * | 1/1913 | Buckner | A61M 3/0283 604/41 |
| 1,531,213 A * | 3/1925 | Nimmer | A61M 3/0279 604/249 |
| 1,593,832 A * | 7/1926 | Larson | A61M 3/0279 604/104 |
| 1,750,272 A * | 3/1930 | Kirk | A61M 29/00 219/227 |
| 2,137,710 A | 11/1938 | Anderson | |
| 2,499,045 A * | 2/1950 | Walker | A61M 29/02 604/103.02 |
| 3,782,381 A | 1/1974 | Winnie | |
| 4,013,080 A | 3/1977 | Froning | |
| 4,136,695 A | 1/1979 | Dafoe | |
| 4,235,234 A | 11/1980 | Whitney et al. | |
| 4,349,023 A | 9/1982 | Gross | |
| 4,511,356 A | 4/1985 | Froning et al. | |
| 4,578,061 A | 3/1986 | Lemelson | |
| 4,684,369 A | 8/1987 | Wildemeersch | |
| 4,710,176 A | 12/1987 | Quick | |
| 4,759,746 A | 7/1988 | Straus | |
| 4,841,977 A | 6/1989 | Griffith et al. | |
| 4,846,799 A | 7/1989 | Tanaka et al. | |
| 4,872,456 A | 10/1989 | Hasson | |
| 5,026,350 A | 6/1991 | Tanaka et al. | |
| 5,100,383 A | 3/1992 | Lichtenstein | |
| 5,116,615 A | 5/1992 | Gokcen et al. | |
| 5,152,749 A | 10/1992 | Giesy et al. | |
| 5,304,141 A | 4/1994 | Johnson et al. | |
| 5,308,358 A | 5/1994 | Bond et al. | |
| 5,318,040 A | 6/1994 | Kensey et al. | |
| 5,354,279 A | 10/1994 | Hofling | |
| 5,360,416 A | 11/1994 | Ausherman et al. | |
| 5,419,777 A | 5/1995 | Hofling | |
| 5,423,770 A | 6/1995 | Yoon | |
| 5,464,395 A | 11/1995 | Faxon et al. | |
| 5,507,796 A | 4/1996 | Hasson | |
| 5,556,376 A | 9/1996 | Yoon | |
| 5,571,083 A | 11/1996 | Lemelson | |
| 5,588,960 A | 12/1996 | Edwards et al. | |
| 5,628,734 A | 5/1997 | Hatfalvi | |
| 5,672,153 A | 9/1997 | Lax et al. | |
| 5,672,174 A | 9/1997 | Gough et al. | |
| 5,683,384 A | 11/1997 | Gough et al. | |
| 5,728,143 A | 3/1998 | Gough et al. | |
| 5,810,804 A | 9/1998 | Gough et al. | |
| 5,827,276 A | 10/1998 | LeVeen et al. | |
| 5,855,576 A | 1/1999 | LeVeen et al. | |
| 5,863,290 A | 1/1999 | Gough et al. | |
| 5,893,839 A | 4/1999 | Johnson | |
| 5,899,909 A | 5/1999 | Claren et al. | |
| 5,964,740 A | 10/1999 | Ouchi | |
| 5,989,266 A | 11/1999 | Foster | |
| 6,009,877 A | 1/2000 | Edwards | |
| 6,016,452 A | 1/2000 | Kasevich | |
| 6,024,726 A | 2/2000 | Hill | |
| 6,056,744 A | 5/2000 | Edwards | |
| 6,059,780 A | 5/2000 | Gough et al. | |
| 6,071,230 A | 6/2000 | Henalla | |
| 6,080,150 A | 6/2000 | Gough | |
| 6,129,726 A | 10/2000 | Edwards et al. | |
| 6,200,302 B1 | 3/2001 | Johnson | |
| 6,203,533 B1 | 3/2001 | Ouchi | |
| 6,210,377 B1 | 4/2001 | Ouchi | |
| 6,210,378 B1 | 4/2001 | Ouchi | |
| 6,217,554 B1 | 4/2001 | Green | |
| 6,231,591 B1 | 5/2001 | Desai | |
| 6,273,852 B1 | 8/2001 | Lehe et al. | |
| 6,277,094 B1 | 8/2001 | Schendel | |
| 6,302,870 B1 | 10/2001 | Jacobsen et al. | |
| 6,302,875 B1 | 10/2001 | Makower et al. | |
| 6,319,230 B1 | 11/2001 | Palasis et al. | |
| 6,425,887 B1 | 7/2002 | McGuckin et al. | |
| 6,432,092 B2 | 8/2002 | Miller | |
| 6,454,765 B1 | 9/2002 | Leveen et al. | |
| 6,461,296 B1 | 10/2002 | Desai | |
| 6,468,273 B1 | 10/2002 | Leveen et al. | |
| 6,470,219 B1 | 10/2002 | Edwards et al. | |
| 6,478,727 B2 | 11/2002 | Seetbon | |
| 6,491,703 B1 | 12/2002 | Ulmsten | |
| 6,494,887 B1 | 12/2002 | Kaladelfos | |
| 6,506,178 B1 | 1/2003 | Schubart et al. | |
| 6,520,927 B1 | 2/2003 | Unsworth | |
| 6,544,230 B1 | 4/2003 | Flaherty et al. | |
| 6,572,593 B1 | 6/2003 | Daum | |
| 6,575,967 B1 | 6/2003 | Leveen et al. | |
| 6,592,559 B1 | 7/2003 | Pakter et al. | |
| 6,595,958 B1 | 7/2003 | Mickley | |
| 6,616,626 B2 | 9/2003 | Crank et al. | |
| 6,638,210 B2 | 10/2003 | Berger | |
| 6,685,648 B2 | 2/2004 | Flaherty et al. | |
| 6,695,855 B1 | 2/2004 | Gaston | |
| 6,702,744 B2 | 3/2004 | Mandrusov et al. | |
| 6,706,017 B1 | 3/2004 | Dulguerov | |
| 6,726,677 B1 | 4/2004 | Flaherty et al. | |
| 6,730,061 B1 | 5/2004 | Cuschieri et al. | |
| 6,802,807 B2 | 10/2004 | Anderson et al. | |
| 6,875,219 B2 | 4/2005 | Arramon et al. | |
| 6,905,480 B2 | 6/2005 | McGuckin, Jr. et al. | |
| 6,911,003 B2 | 6/2005 | Anderson et al. | |
| 6,932,759 B2 | 8/2005 | Kammerer et al. | |
| 6,939,322 B2 | 9/2005 | Crank et al. | |
| 6,989,004 B2 | 1/2006 | Hinchliffe et al. | |
| 6,994,693 B2 | 2/2006 | Tal | |
| 7,014,607 B2 | 3/2006 | Gellman | |
| 7,087,040 B2 | 8/2006 | McGuckin, Jr. et al. | |
| 7,106,574 B2 | 9/2006 | Beyerlein | |
| 7,120,487 B2 | 10/2006 | Nelson | |
| 7,172,576 B2 | 2/2007 | Sawa et al. | |
| 7,179,257 B2 | 2/2007 | West et al. | |
| 7,282,020 B2 | 10/2007 | Kaplan | |
| 7,648,500 B2 | 1/2010 | Edwards et al. | |
| 2001/0037086 A1 | 11/2001 | Gambale et al. | |
| 2002/0082546 A1 | 6/2002 | Crank et al. | |
| 2002/0173689 A1 | 11/2002 | Kaplan | |
| 2003/0032929 A1 | 2/2003 | McGuckin, Jr. | |
| 2003/0055400 A1 | 3/2003 | Seward et al. | |
| 2003/0130575 A1 | 7/2003 | Desai | |
| 2003/0149440 A1 | 8/2003 | Kammerer et al. | |
| 2003/0161824 A1 | 8/2003 | Rackley et al. | |
| 2003/0171644 A1 | 9/2003 | Anderson et al. | |
| 2003/0176762 A1 | 9/2003 | Kammerer | |
| 2003/0187382 A1 | 10/2003 | Unsworth | |
| 2003/0216693 A1 | 11/2003 | Mickley | |
| 2004/0002647 A1 | 1/2004 | Desai | |
| 2004/0039338 A1 | 2/2004 | Lee et al. | |
| 2004/0064098 A1 | 4/2004 | Cuschieri et al. | |
| 2004/0068242 A1 | 4/2004 | McGuckin, Jr. | |
| 2004/0068286 A1 * | 4/2004 | Mendius | A61B 17/12099 606/191 |
| 2004/0092865 A1 | 5/2004 | Flaherty et al. | |
| 2004/0097974 A1 | 5/2004 | De Leval | |

(56) References Cited

U.S. PATENT DOCUMENTS

| | | |
|---|---|---|
| 2004/0106845 A1 | 6/2004 | Anderson et al. |
| 2004/0106846 A1 | 6/2004 | Gellman |
| 2004/0176726 A1 | 9/2004 | Katoh et al. |
| 2004/0254541 A1 | 12/2004 | Wong et al. |
| 2004/0260240 A1 | 12/2004 | Beyerlein |
| 2005/0004563 A1 | 1/2005 | Racz et al. |
| 2005/0065395 A1 | 3/2005 | Mellier |
| 2005/0101909 A1 | 5/2005 | Rossi |
| 2005/0113686 A1 | 5/2005 | Peckham |
| 2005/0245787 A1 | 11/2005 | Cox et al. |
| 2005/0255039 A1 | 11/2005 | Desai |
| 2005/0261667 A1 | 11/2005 | Crank et al. |
| 2006/0025720 A1 | 2/2006 | Sawa et al. |
| 2006/0064062 A1 | 3/2006 | Gurusamy et al. |
| 2006/0129101 A1 | 6/2006 | McGuckin, Jr. |
| 2006/0135915 A1 | 6/2006 | Tucker |
| 2006/0135916 A1 | 6/2006 | Tucker |
| 2006/0189940 A1 | 8/2006 | Kirsch |
| 2006/0199990 A1 | 9/2006 | Rioux et al. |
| 2006/0206116 A1 | 9/2006 | Yeung |
| 2006/0247600 A1 | 11/2006 | Yeung et al. |
| 2006/0265043 A1 | 11/2006 | Mandrusov et al. |
| 2011/0009848 A1 | 1/2011 | Woodard et al. |

FOREIGN PATENT DOCUMENTS

| | | |
|---|---|---|
| WO | WO 96/16606 | 6/1996 |
| WO | WO 2006/027549 A1 | 3/2006 |

OTHER PUBLICATIONS

Gupta, Sanjay et al., "Technical Innovation: Using a Coaxial Technique with a Curved Inner Needle for CT-Guided Fine-Needle Aspiration Biopsy", AJR, Jul. 2002, vol. 170, pp. 109-112.

Medtronic Therapy/EP Systems, Transseptal Sheaths/Needles, http://www.medtronic.com/epsystems/trans_sheaths_needles.html, retrieved Jan. 2, 2007, pp. 1-4.

* cited by examiner

DILATION CAP FOR ENDOLUMINAL DEVICE

CROSS-REFERENCE TO RELATED APPLICATIONS

This application claims priority and the benefit of provisional U.S. Patent Application Ser. No. 61/605,934, filed Mar. 2, 2012, which is incorporated herein by reference in its entirety.

TECHNICAL FIELD

This disclosure relates generally to medical devices. More specifically, this disclosure relates to a dilation cap for an endoluminal medical device such as a fluid injection device for the treatment of stress urinary incontinence.

BACKGROUND

Various medical procedures involve the introduction of a medical device into a body lumen. Some of these procedures may involve penetrating the wall of the body lumen, for example, to inject a therapeutic agent into the wall of the body lumen or the tissue surrounding the body lumen. Such a procedure may be used to treat stress urinary incontinence (SUI).

SUI is a urological disorder that exists in relatively large numbers of the human population and typically exists in older patients. Patients suffering from SUI often are unable to control and prevent the release of urine from the urethra, specifically in times of coughing, sneezing, laughing, or exercise. SUI may be caused by the weakening of muscle tissues, such as muscle tissues and fascia that coaxially surround the urethra. SUI also may be caused by weakening of bladder tissues, or a weakening or malfunction of the sphincter muscles at the bladder neck. Female patients have been known to suffer from SUI following pregnancy or a urological surgical procedure. Several treatments are known to eliminate or minimize the effects of SUI, such as installing a pessary into the female patient's vagina, installing a urethral sling into a patient, or injecting bulking agents into the patient's tissue surrounding the urethra.

In any procedure involving penetration of the wall of a body lumen, tenting or stretching of the luminal wall may occur during attempted penetration of the wall. Such tenting may increase the force that may be required to penetrate the wall with the cutting device, such as a needle. Such tenting also may reduce the accuracy with which the penetration may be performed.

SUMMARY

The present embodiments provide a dilation cap for an endoluminal medical device such as a fluid injection device for the treatment of stress urinary incontinence.

In one example, a dilation cap configured to be coupled to an elongate cannula of a medical device may include a distal tip, an intermediate body, and a proximal coupling member. The distal tip may at least partially surround a longitudinal axis of the dilation cap. The distal tip may include a cavity configured to receive a distal end of the elongate cannula of the medical device. The intermediate body may extend proximally from the distal tip. The intermediate body may include a dilator portion. The dilator portion may include a projection extending laterally in a direction away from the longitudinal axis of the dilation cap. The proximal coupling member may extend proximally from the intermediate body. The proximal coupling member may at least partially surround the longitudinal axis of the dilation cap. The proximal coupling member may be configured to engage an intermediate portion of the elongate cannula of the medical device. The intermediate body may be asymmetrical with respect to the longitudinal axis of the dilation cap.

In another example, a system configured to be introduced into a body lumen of a patient may include a medical device and a dilation cap. The medical device may include an elongate cannula extending along a longitudinal axis and having a distal end and an intermediate portion positioned proximal of the distal end. The dilation cap may be removably coupled to the elongate cannula of the medical device. The dilation cap may include a distal tip, an intermediate body, and a proximal coupling member. The distal tip may include a cavity. The distal end of the elongate cannula may be received within the cavity of the distal tip. The intermediate body may extend proximally from the distal tip. The intermediate body may include a dilator portion. The dilator portion may include a projection extending laterally in a direction away from the longitudinal axis of the elongate cannula. The proximal coupling member may extend proximally from the intermediate body. The proximal coupling member may at least partially surround the intermediate portion of the elongate cannula to retain the dilation cap in place relative to the elongate cannula.

In another example, a method of dilating a body lumen may include introducing a dilation cap into the body lumen. The dilation cap may be removably attached to a medical device. The medical device may include an elongate cannula extending along a longitudinal axis. The dilation cap may include a distal tip, an intermediate body, and a proximal coupling member. The distal tip may include a cavity configured to receive a distal end of the elongate cannula of the medical device. The intermediate body may extend proximally from the distal tip and may include a dilator portion. The proximal coupling member may extend proximally from the intermediate body. The proximal coupling member may at least partially surround the intermediate portion of the elongate cannula to retain the dilation cap in place relative to the elongate cannula. The method may include engaging a wall of the body lumen with a projection of the dilator portion of the dilation cap. The projection may extend laterally in a direction away from the longitudinal axis of the elongate cannula. Engaging the wall of the body lumen with the projection may include engaging a first circumferential segment of the wall of the body lumen to push the distal end of the elongate cannula of the medical device toward a second circumferential segment of the wall of the body lumen opposite the first circumferential segment.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

DETAILED DESCRIPTION OF THE DRAWINGS AND THE PRESENTLY PREFERRED EMBODIMENTS

Detailed embodiments of the present invention are disclosed herein. It is understood, however, that the disclosed embodiments are merely exemplary of the invention, which may be embodied in various and alternative forms. The figures are not necessarily to scale, and some figures may be configured to show the details of a particular component. Therefore, specific structural and functional details disclosed herein are not to be interpreted as limiting, but merely as a representative basis for the claims and for teaching one skilled in the art to practice the present invention.

In the present disclosure, the term "proximal" refers to a direction that is generally toward a physician during a medical procedure, while the term "distal" refers to a direction that is generally toward a target site within a patient's anatomy during a medical procedure.

Various medical devices for implantation in a body vessel are disclosed herein. Preferred embodiments relate to a dilation cap for a medical fluid injection device, which may be used to inject fluid into tissue surrounding a body vessel. The medical fluid injection devices are described with respect to an exemplary embodiment useful for injecting fluid into tissue coaxially surrounding a female urethra in an attempt to strengthen and bulk the tissue to prevent or reduce the effects of stress urinary incontinence (SUI). One suitable medical device is described in US Patent Application Pub. No. 2011/0009848 by Woodard et al., which is incorporated herein by reference in its entirety. However, this disclosure is not so limited, and the devices may be used in other portions of the human or mammal anatomy to inject therapeutic agents within the patient. Additionally, the dilation caps described herein may be used with any type of medical device which may be inserted into any type of body lumen (e.g., a urethra, a fallopian tube, a vagina, a nasal cavity, a vessel or cavity of a gastrointestinal tract, or a vessel or cavity of a cardiovascular system).

Figure 1:
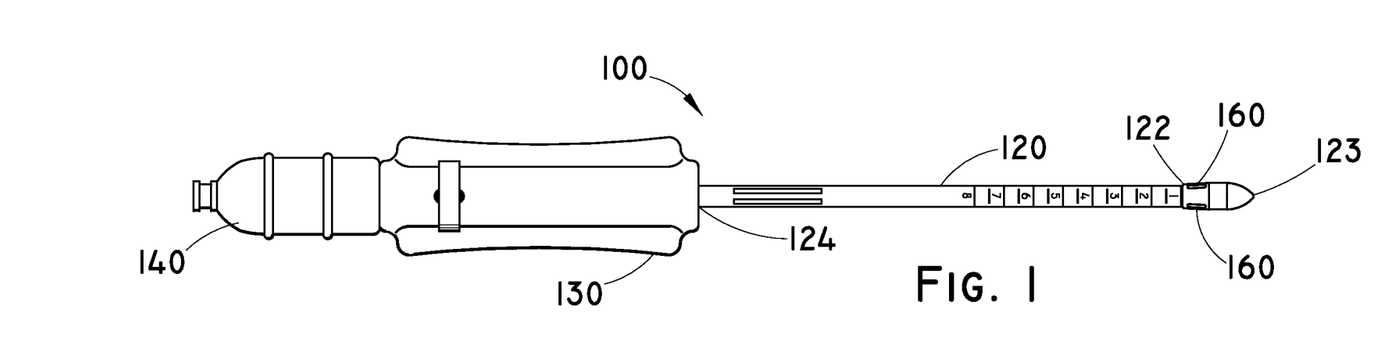
FIG. 1 is a top view of one example of a medical device with each of a plurality of needles disposed within an elongate cannula of the medical device.
Figure 2:
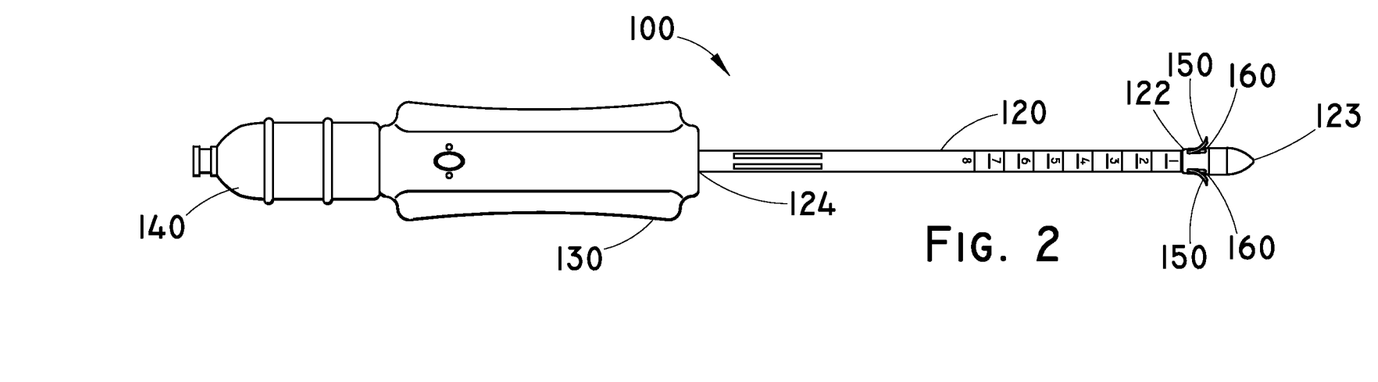
FIG. 2 is a top view of the medical device of FIG. 1 with each of the plurality of needles extended outward from the elongate cannula.
Figure 3:
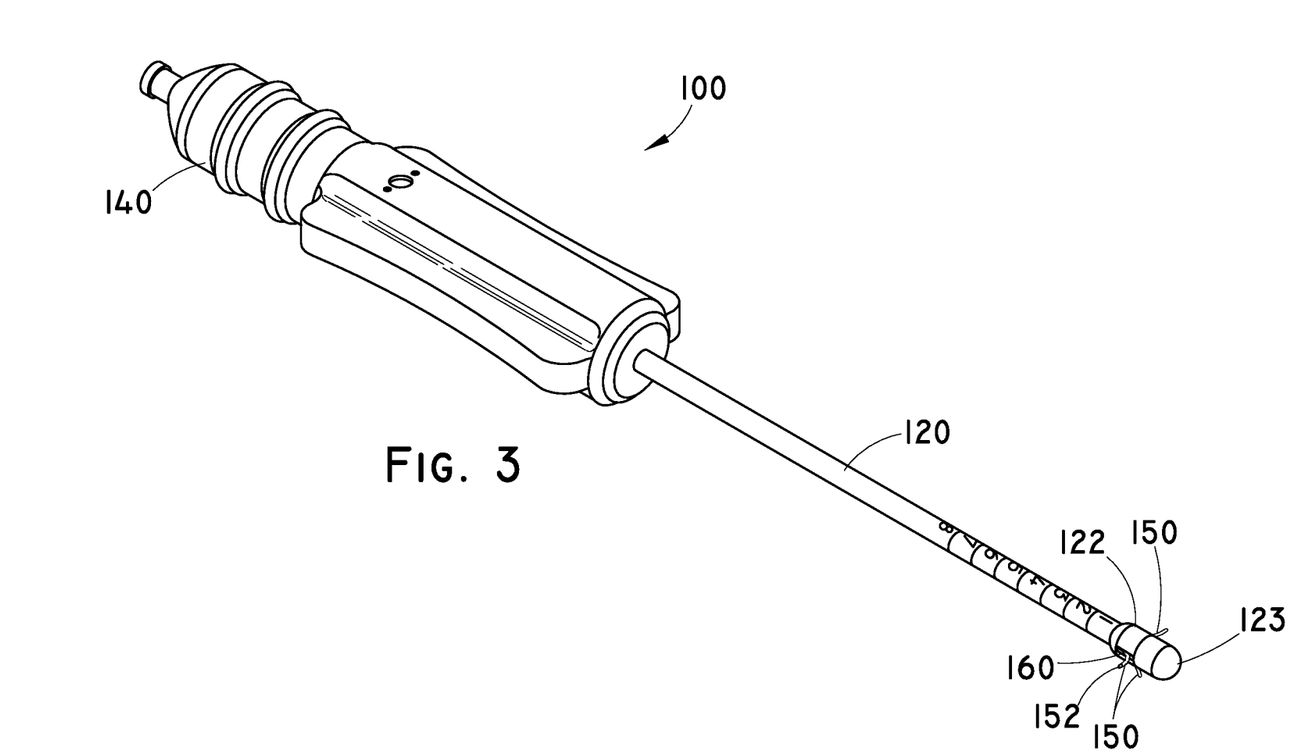
FIG. 3 is a perspective view of the medical device as shown in FIG. 2.

FIGS. 1-3 illustrate one embodiment of a medical device 100 configured as a fluid injection device, which may be suitable for various medical procedures. In one example, the medical device 100 may be suitable for injecting therapeutic agents (e.g., bulking agents, stem cell based media or agents, or other injection media) into the tissue coaxially surrounding a female urethra in an attempt to strengthen and bulk the tissue to prevent or reduce the effects of SUI. In other examples, the medical device 100 may be used in other portions of the human or mammal anatomy. For example, the medical device 100 may be used to inject a therapeutic agent into tissue surrounding a lumen or cavity within the body or to inject a therapeutic agent into a wall of a body vessel. The medical device 100 may be inserted into a patient through an available orifice, such as directly into the female urethra. Alternatively, the medical device 100 may be inserted into the patient percutaneously. Although the medical device 100 will generally be discussed with reference to embodiments configured for insertion into a patient's urethra, the medical device may be otherwise sized and shaped to be configured for other anatomical locations and procedures without departing from the scope of this disclosure.

The medical device 100 may include an elongate cannula 120, a first handle 130 that is fixed to a portion of the elongate cannula, and a second handle 140 that is movably disposed with respect to the first handle. A plurality of needles 150 may be movably disposed within a lumen extending longitudinally within the elongate cannula 120. Each of the plurality of needles 150 may be fixed to the second handle 140. The second handle 140 may be translated longitudinally relative to the first handle 130 to cause the plurality of needles 150 to translate longitudinally within the lumen of the elongate cannula 120. The elongate cannula 120 may include a distal end portion 122. A plurality of apertures 160 may be disposed through the distal end portion 122 of the elongate cannula 120 to provide communication with the lumen of the elongate cannula. Each of the plurality of needles 150 may be disposed within the elongate cannula 120 to be aligned with a respective one of the plurality of apertures 160. When the second handle 140 is disposed in a first position relative to the first handle, as shown in FIG. 1, the distal tip 152 of each of the plurality of needles 150 may be disposed within a corresponding aperture 160 just inside of the outer circumferential surface of the elongate cannula 120. When the second handle 140 is translated longitudinally with respect to the first handle 130 into a second position, as shown in FIGS. 2-3, the distal tip 152 of each of the plurality of needles 150 may extend outward from the corresponding aperture 160 and the outer circumferential surface of the elongate cannula 120 to engage (e.g., to penetrate) tissue proximate to the distal end portion 122 of the elongate cannula 120. In other examples, the medical device may include any number of apertures, and any type of piercing or cutting device may be configured to extend from the apertures.

The elongate cannula 120 may be an elongate flexible member that spans between the distal end portion 122 and a proximal end portion 124. In one example, the elongate cannula 120 may have a length of between about 8 and about 25 cm, typically about 16.5 cm. In other examples, the elongate cannula 120 may have any suitable length. The length of the elongate cannula 120 may be configured to access a desired location within a body lumen. The lumen of the elongate cannula 120 may extend from an open proximal end positioned at the proximal end portion 124 of the elongate cannula to a closed distal terminus 123 positioned at the distal end portion 122 of the elongate cannula. In some embodiments, the distal end portion 122 may be configured as a bulb or closed tube that is connected to, or formed integrally with, the distal end of the elongate cannula 120 as shown in FIGS. 1-3. The bulb may include a lumen in communication with the lumen of the elongate cannula 120 when the bulb is fixed to the distal end of the elongate cannula.

Figure 4:
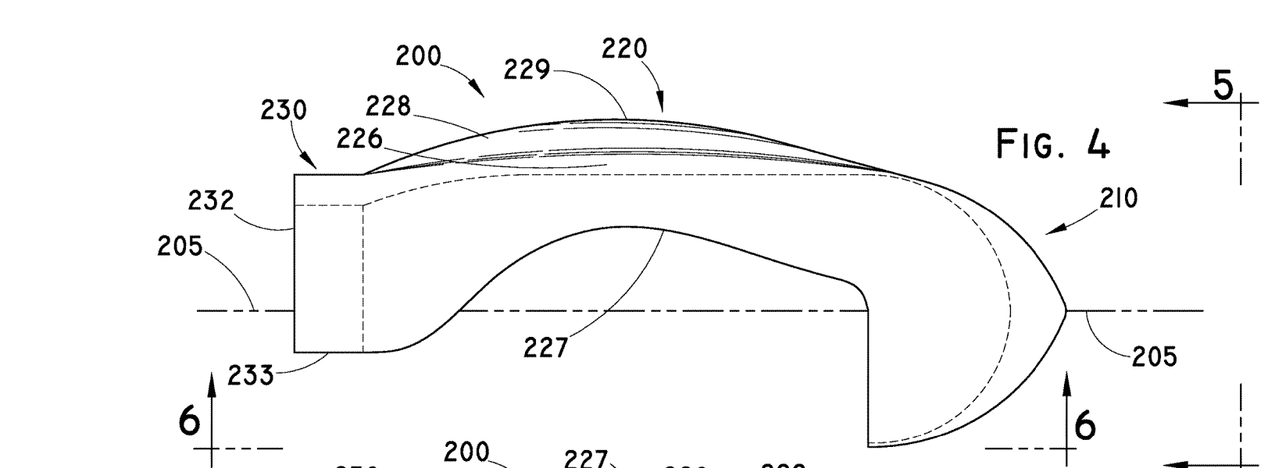
FIG. 4 is a side view of one example of a dilation cap configured to be coupled to a medical device.
Figures 5, 8:
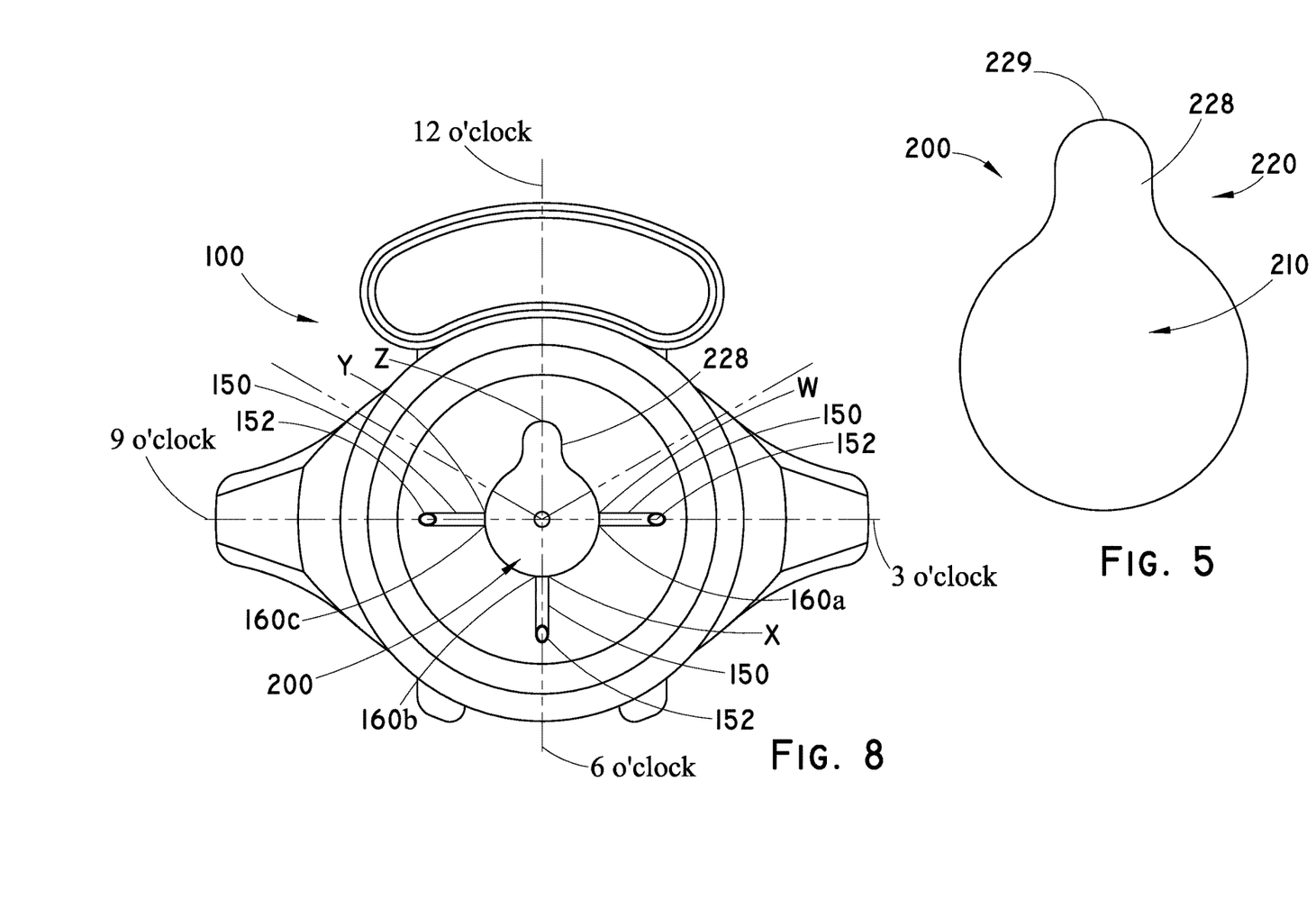
FIG. 5 is a front view of the dilation cap of FIG. 4.
FIG. 8 is a front view of the dilation cap of FIGS. 4-6 removably coupled to the medical device of FIGS. 1-3.
Figure 6:
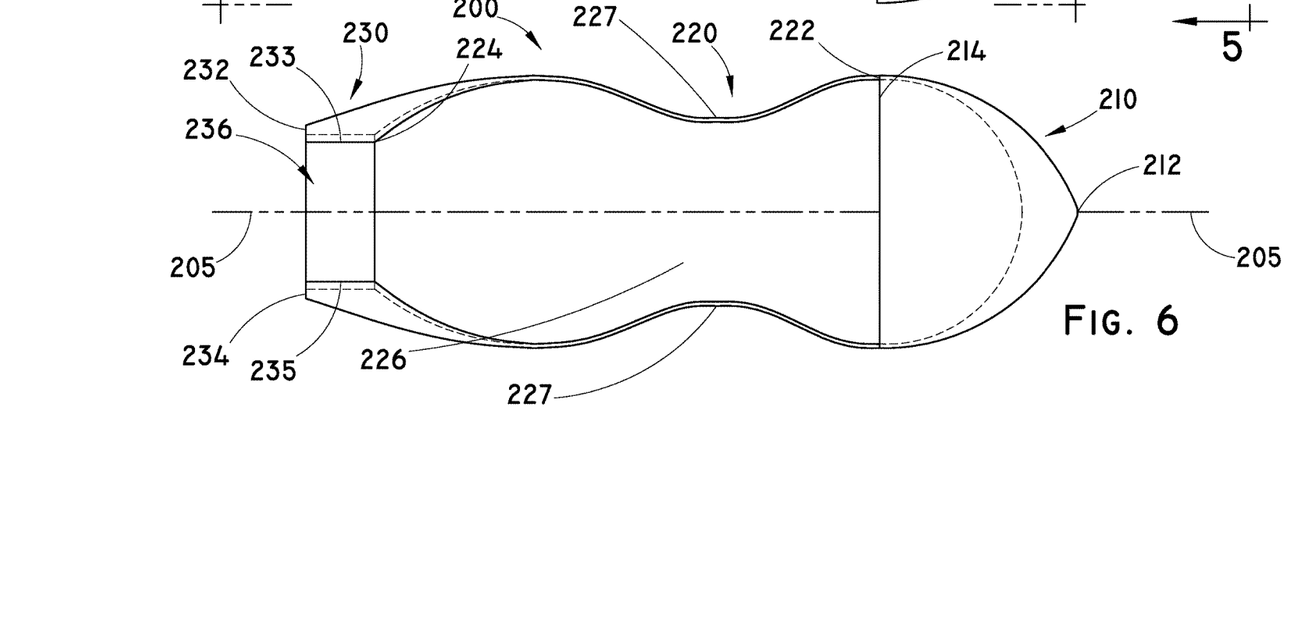
FIG. 6 is a bottom view of the dilation cap of FIGS. 4-5.

FIGS. 4-6 illustrate one embodiment of a dilation cap 200, which may be coupled to a medical device as further described below. The dilation cap 200 may include a distal tip 210, an intermediate body 220, and a proximal coupling member 230. The distal tip 210 may at least partially surround the longitudinal axis 205 of the dilation cap 200 to form a cavity within the distal tip. In other words, the distal tip 210 may be at least partially hollow with a cavity formed therein. The cavity may be configured to receive an elongate cannula of a medical device as further described below. In one example, the distal tip 210 may include a distal end 212 and a proximal end 214. The proximal end 214 may be configured as a band or ring surrounding the longitudinal axis 205 of the dilation cap 200. In one example, a cross section of the proximal end 214 may have a round or circular shape. In other examples, the cross section of the proximal end may have an elliptical, rectangular, triangular, or any other polygonal or non-polygonal shape. The cross-sectional shape of the proximal end may be configured to correspond to the cross sectional shape of the elongate cannula of the medical device. The proximal end 214 may be an open end in communication with the cavity of the distal tip 210. The distal end 212 may be a closed end of the distal tip 210. The distal end 212 may have a cross sectional area that is smaller than the cross sectional area of the proximal end 214. The cross sectional area of the distal tip 210 may reduce gradually from the proximal end 214 to the distal end 212. The distal tip 210 may be configured as an atraumatic tip or contoured nose to minimize pain or discomfort to the patient upon introduction of the dilation cap 200 into the patient's body. To that end, the distal tip 210 may have a rounded, domed, tapered, or other atraumatic shape. The distal tip 210 may be sized and shaped to aid in advancing the dilation cap 200 within a body lumen. In one example, the proximal end 214 of the distal tip 210 may have an outside diameter between about 4 and about 12 mm, typically about 8 mm. In another example, the distal tip 210 may have a length between about 11 and about 31 mm, typically about 21 mm. In other examples, the distal tip may have any size or shape suitable for introduction into a body lumen.

The intermediate body 220 may extend proximally from the distal tip 210. The intermediate body 220 may have a distal end 222, which may be attached to the distal tip 210, and a proximal end 224, which may be attached to the proximal coupling member 230. In other words, the distal tip 210 and the proximal coupling member 230 may be coupled to one another by the intermediate body 220. In one example, the intermediate body 220 may include a rib 226 extending between the distal end 222 and the proximal end 224. The rib 226 may extend longitudinally and partially circumferentially with respect to the longitudinal axis 205 of the dilation cap 200. The rib 226 may include one or more narrowed portions, which may be configured to align with the apertures 160 and/or the needles 150 of the medical device 100 as further described below. The narrowed portions may be portions of the rib having a narrower width than other portions of the rib 226. For example, the narrowed portion may be formed by two indentations 227 positioned on opposing sides of the rib 226 as shown in FIGS. 4 and 6. The longitudinal segment of the rib 226 including the indentations 227 may have a narrower width than the longitudinal segments of the rib positioned proximal and/or distal of the indentations. In one example, the rib 226 of the intermediate body 220 may have a width between about 1 and about 6 mm, typically between about 2 and about 4 mm. Additionally, or alternatively, the rib 226 may have a length between about 8 and about 30 mm, typically between about 18 and about 20 mm. In other examples, the rib may have any size or shape suitable for introduction into a body lumen.

The intermediate body 220 may include a dilator portion, which may be configured to dilate a body lumen as further described below. To that end, the dilator portion may include a contoured outer surface. The distance between the contoured outer surface of the dilator portion and the longitudinal axis 205 of the dilation cap 200 may vary longitudinally and/or circumferentially along the contoured surface. The contoured surface may define a bump, a hill, a dome, an arch, or any other type of protrusion extending laterally away from the longitudinal axis 205 of the dilation cap 200.

In one example, the dilator portion may include a projection 228 extending laterally in a direction away from the longitudinal axis 205 of the dilation cap 200. The projection 228 may be configured as a dilation keel extending longitudinally along the intermediate body 220 and laterally away from the longitudinal axis 205 of the dilation cap 200 as shown in FIGS. 4-5. The projection 228 may include a rounded outer edge as best shown in FIG. 5. In other words, a cross section of the projection 228 may have an arched shape defining the rounded outer edge. Such a rounded outer edge may provide a substantially atraumatic edge, which may reduce the potential for pain or discomfort to the patient upon introduction of the dilation cap 200 into a body lumen as further described below. The outer edge may be positioned opposite an inner edge, which may be attached to the rib 226. In one example, the projection 228 of the intermediate body 220 may have a thickness between about 1 and about 6 mm, typically between about 2 and about 4 mm. Additionally, or alternatively, the projection 228 may have a length between about 8 and about 30 mm, typically between about 18 and about 20 mm. Additionally, or alternatively, the projection 228 may have a height between about 1 and about 9 mm, typically between about 2 and about 6 mm. The height of the projection 228 may vary longitudinally along the length of the projection as further described below. In other examples, the projection may have any size or shape suitable for introduction into a body lumen.

The projection 228 may include a spine 229 extending longitudinally along the outer edge of the projection. The spine 229 may extend longitudinally adjacent to the rib 226. The spine 229 may be substantially coplanar with the longitudinal axis 205 of the dilation cap 200 as shown in FIGS. 4-5. Alternatively, the spine 229 may be configured such that the spine and the longitudinal axis 205 of the dilation cap 200 are not coplanar with one another. In one example, the outer edge of the projection 228 may be curved in a longitudinal direction such that the spine 229 extends longitudinally and laterally. In other words, the distance between the spine 229 and the longitudinal axis 205 of the dilation cap 200 may vary longitudinally along a length of the projection 228. In this manner, the height of the projection 228 may vary along the length of the projection. The spine 229 may be configured as a curve or an arc positioned on the plane intersecting the spine and the longitudinal axis 205 of the dilation cap 200. In one example, the distance between the spine 229 and the longitudinal axis 205 of the dilation cap 200 may increase from a distal end of the projection 228 to an intermediate portion of the projection and decrease from the intermediate portion to a proximal end of the projection. A portion of the spine 229 corresponding to the intermediate portion of the projection 228 may be substantially parallel to the longitudinal axis 205 of the dilation cap 200. Additionally, or alternatively, the cross sectional area of the projection 228 may vary longitudinally along the length of the projection. In one example, the cross sectional area of the projection 228 may increase from the distal end of the projection to the intermediate point of the projection and decrease from the intermediate point to the proximal end of the projection. The intermediate portion of the projection may be configured as an apex, or an outermost portion of the dilation cap 200. The spine 229 may define the outermost edge of the intermediate body 220 and/or the dilation cap 200. In other words, the spine 229 may be positioned a greater distance laterally from the longitudinal axis 205 of the dilation cap 200 than any other portion of the dilation cap.

The projection 228 may be configured such that a transverse cross section of the dilator portion of the intermediate body 220 has an eccentric shape with respect to the longitudinal axis 205 of the dilation cap 200. In other words, the projection 228 may be offset with respect to the longitudinal axis 205 of the dilation cap 200 such that the intermediate body 220 is not symmetrical (i.e., asymmetrical) about the longitudinal axis. The center of the eccentric or offset projection 228 may be offset from or misaligned with the longitudinal axis 205. In other words, the projection 228 may be positioned on an outer surface of the rib 226 away from the longitudinal axis 205. The projection 228 may be configured to extend away from the longitudinal axis 205 in a first direction, and the dilation cap 200 may be free of any corresponding portion extending away from the longitudinal axis in a second direction opposite of the first direction so that the dilator portion has an eccentric shape. In this manner, the dilation cap 200 may impose a greater outward force on a circumferential segment of a body lumen aligned with the projection 228 than on another circumferential segment of the body lumen misaligned with the projection 228 as further described below.

The proximal coupling member 230 may extend proximally from the intermediate body 220. The proximal coupling member 230 may at least partially surround the longitudinal axis 205 of the dilation cap 200. The proximal coupling member 230 may be configured to engage an intermediate portion of an elongate cannula of a medical device as further described below. In one example, the proximal coupling member 230 may be a substantially C-shaped member as shown in FIGS. 4 and 6. A plurality of arms may cooperatively define the C-shaped member. For example, the proximal coupling member 230 may include a first arm 232 and a second arm 234 collectively defining the C-shaped member. Each of the first and second arms 232, 234 may define a portion (e.g., approximately half) of the C-shaped member. The first arm 232 may extend at least partially circumferentially around the longitudinal axis 205 of the dilation cap 200 in a first circumferential direction. The second arm 234 may extend at least partially circumferentially around the longitudinal axis 205 of the dilation cap 200 in a second circumferential direction opposite the first circumferential direction. The first and second arms 232, 234 may be coupled to one another to form the proximal coupling member 230.

The first arm 232 of the proximal coupling member 230 may include a coupled end and a free end 233 opposite the coupled end. The second arm 234 of the proximal coupling member 230 may include a coupled end and a free end 235 opposite the coupled end. The coupled ends of the first and second arms 232, 234 may be coupled to one another. The first and second arms 232, 234 may be formed separately or integrally with one another. The free end 233 of the first arm 232 may be positioned adjacent to the free end 235 of the second arm 234 to define an aperture 236 between the free end 233 and the free end 235 as shown in FIG. 6. The aperture 236 may be configured as an entrance or mouth of an opening positioned within the C-shaped proximal coupling member 230. In one example, the proximal coupling member 230 may have an outside diameter between about 2.5 and about 8 mm, typically about 5.25 mm. Additionally, or alternatively, the proximal coupling member 230 may have a length between about 1 and about 9 mm, typically between about 2 and about 6 mm. In other examples, the proximal coupling member may have any size or shape suitable for introduction into a body lumen.

The first and second arms 232, 234 may be movable relative to one another to manipulate the aperture 236. For example, the first and second arms 232, 234 may be movable between a contracted configuration and an expanded configuration. In the contracted configuration, the aperture 236 defined by the first and second arms 232, 234 may have a contracted diameter. In other words, the free end 233 of the first arm 232 and the free end 235 of the second arm 234 may be separated by a contracted distance. In the expanded configuration, the aperture 236 defined by the first and second arms 232, 234 may have an expanded diameter that is larger than the contracted diameter. In other words, the free end 233 of the first arm 232 and the free end 235 of the second arm 234 may be separated by an expanded distance that is greater than the contracted distance. In one example, the contracted configuration may be a relaxed configuration, and the expanded configuration may be a strained configuration. In other words, the first and second arms 232, 234 may be biased toward the relaxed, or contracted, configuration. To that end, the first and second arms 232, 234 of the proximal coupling member 230 may be formed from a shape memory or a superelastic material that is capable of returning to a predefined shape following deformation. The first and second arms 232, 234 may be movable between the contracted configuration and the expanded configuration to engage a medical device. In this manner, the proximal coupling member 230 may be configured as a snap ring or clip, which may be capable of engaging a medical device as further described below.

The dilation cap 200 may be formed from any suitable material as further described below. In one example, the dilation cap 200 may be formed from acrylonitrile butadiene styrene (ABS). This may enable the dilation cap 200 to have relatively high rigidity and/or mechanical strength. Additionally, or alternatively, the dilation cap 200 or portions thereof (e.g., the projection 228) may be substantially non-expandable.

Figure 7:
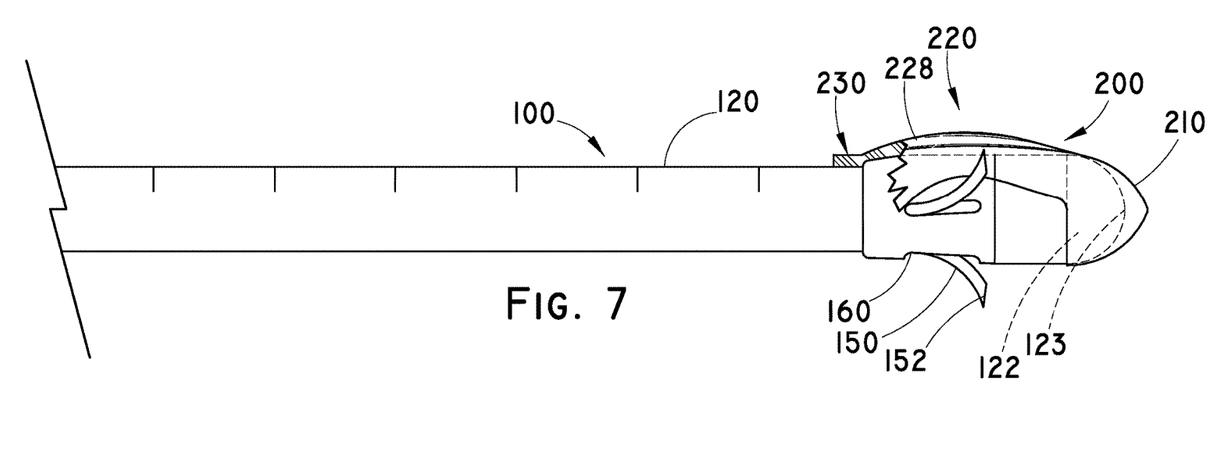
FIG. 7 illustrates the dilation cap of FIGS. 4-6 removably coupled to the medical device of FIGS. 1-3.

FIGS. 7-8 illustrate the dilation cap 200 coupled to the medical device 100. The distal terminus 123 of the distal end portion 122 of the medical device 100 may be received within the cavity of the distal tip 210 of the dilation cap 200 as shown in FIG. 7. An inner surface of the distal tip 210 of the dilation cap 200, which may define the cavity, may engage an outer surface of the distal terminus 123 of the medical device 100. To that end, the cavity of the distal tip 210 of the dilation cap 200 may be sized and shaped to correspond to the size and shape of the distal terminus 123 of the medical device 100. The medical device 100 and the dilation cap 200 may be substantially coaxial such that the longitudinal axis of the elongate cannula 120 may be substantially collinear with the longitudinal axis 205 of the dilation cap 200.

The intermediate body 220 of the dilation cap 200 may extend longitudinally and at least partially circumferentially along the elongate cannula 120 of the medical device 100. An inner surface of the intermediate body 220 (e.g., an inner surface of the rib 226) may engage an outer surface of the elongate cannula 120. For example, the inner surface of the intermediate body 220 may engage the outer surface of the distal portion 122 of the elongate cannula 120. The dilator portion (e.g., the projection 228) of the dilation cap 200 may be substantially longitudinally aligned with the apertures 160 of the medical device 100. Additionally, or alternatively, the dilator portion of the dilation cap 200 may be circumferentially misaligned with the apertures 160 as further described below. In other words, the dilator portion of the dilation cap 200 may be positioned generally adjacent to the apertures 160 with respect to the circumference of the elongate cannula 120. Such positioning may aid in dilating a body lumen for injection of a therapeutic agent into a wall of the body lumen as further described below.

The proximal coupling member 230 of the dilation cap 200 may engage the elongate cannula 120 of the medical device 100. The proximal coupling member 230 may engage an intermediate portion of the elongate cannula 120 positioned proximal of the distal portion 122. In one example, the proximal coupling member 230 may be positioned longitudinally proximal of the apertures 160 of the medical device 100. To engage the elongate cannula 120, the proximal coupling member 230 may at least partially surround the elongate cannula. For example, the first arm 232 of the proximal coupling member 230 may extend at least partially circumferentially around the elongate cannula 120 in a first circumferential direction. The second arm 234 of the proximal coupling member 230 may extend at least partially circumferentially around the elongate cannula 120 in a second circumferential direction opposite the first circumferential direction. In this manner, the elongate cannula 120 of the medical device 100 may be received within the opening defined by the first and second arms 232, 234 of the proximal coupling member 230. The first and second arms 232, 234 of the proximal coupling member 230 may impart a radially inward force on the elongate cannula 120 to retain the dilation cap 200 in place relative to the elongate cannula. In other words, the first and second arms 232, 234 may squeeze the elongate cannula 120 between the first and second arms of the proximal coupling member 230 to frictionally engage the elongate cannula.

FIG. 8 shows an end view of the distal end portion 122 of the medical device 100 with the dilation cap 200 coupled to the medical device. In one example, the apertures 160 of the medical device 100 may include a first aperture 160a, a second aperture 160b, and a third aperture 160c. Each of the apertures 160 may be disposed at a different location about the outer circumferential surface of the distal end portion 122 of the medical device 100. In one example, the distal terminus 123 of the elongate cannula 120 may be considered to be the face of a conventional analog clock, and the first aperture 160a may be disposed at about the 3 o'clock position W, the second aperture 160b may be disposed at about the 6 o'clock position X, and the third aperture 160c may be disposed at about the 9 o'clock position Y. No aperture may be provided at about the 12 o'clock position Z as shown in FIG. 8. The first and third apertures 160a, 160c may be substantially equidistant from the second aperture 160b with respect to the outer circumferential surface of the elongate cannula 120. Each of the positions W, X, Y, Z may be spaced from the respective adjacent positions by about ninety degrees. In other examples, the medical device may include any number of apertures disposed at any locations about the circumference of the elongate cannula.

In one example, the outer circumferential surface of the elongate cannula 120 may be divided into four quadrants, each quadrant covering about one fourth of the outer circumferential surface of the elongate cannula. The quadrants may be aligned such that the borders between neighboring quadrants are disposed about midway between the 12 o'clock position Z and the 3 o'clock position W, about midway between the 3 o'clock position W and the 6 o'clock position X, about midway between the 6 o'clock position X and the 9 o'clock position Y, and about midway between the 9 o'clock position Y and the 12 o'clock position Z. The first aperture 160a may be disposed upon the first quadrant, the second aperture 160b may be disposed upon the second quadrant, and the third aperture 160c may be disposed upon the third quadrant. No aperture may be disposed upon the fourth quadrant. In other examples, the outer circumferential surface of the elongate cannula may be divided into any number of segments (e.g., halves, thirds, sextants, octants, or any other segments), and the medical device may include any number of apertures disposed upon any of the segments.

The apertures 160 may be positioned about the circumference of the elongate cannula 120 to accurately position the needles 150 in a desired pattern. In one example, the medical device 100 may be configured to inject bulking solution or other therapeutic agents into the muscular tissue surrounding a female patient's urethra for the treatment or prevention of SUI. It may be desirable to avoid injecting a therapeutic agent through the anterior portion of the urethra (i.e. the portion of the urethra that runs closest to the front of the body) because blood vessels and/or nerve bundles may be disposed proximate to the anterior portion of the urethra. Accordingly, the apertures 160 may be positioned circumferentially about the elongate cannula 120 such that the needles 150 may exit the elongate cannula to substantially simultaneously enter the tissue (e.g., submucosa and/or musculature) coaxially surrounding the urethra but remote from the anterior portion of the urethra. Once the needles 150 pierce and are positioned within the tissue, the medical device 100 may be further manipulated to simultaneously inject therapeutic agents into the tissue via the needles while avoiding injection into the anterior portion of the urethra.

The dilation cap 200 may be positioned on the medical device 100 to correspond with the positions of the apertures 160 and/or the needles 150 of the medical device. For example, the projection 228 of the dilation cap 200 may be positioned at approximately the 12 o'clock position Z as shown in FIG. 8. Additionally, or alternatively, the projection 228 of the dilation cap 200 may be positioned upon the fourth quadrant. The projection 228 may be positioned to correspond with a circumferential position where no aperture 160 or needle 150 is provided. The projection 228 may extend laterally in a direction away from the second aperture 160b. In this manner, the dilation cap 200 may be configured such that the projection 228 does not interfere with the operation of the medical device 100 (e.g., extension of the needles 150 from the apertures 160).

Additionally, or alternatively, the indentations 227 of the dilation cap 200 may be positioned at approximately the 3 o'clock position W and the 9 o'clock position Y. In other words, the indentations 227 may be positioned to correspond with circumferential positions where apertures 160 and/or needles 150 are provided. In one example, the indentations 227 may be positioned adjacent to the first aperture 160a and the third aperture 160c. Upon extension of the needles 150 through the apertures, a needle may extend out the first aperture 160a and through an indentation 227 approximately in the direction W, and another needle may extend out the third aperture 160c and through another indentation 227 approximately in the direction Y. In this manner, the dilation cap 200 may be configured such that the intermediate body 220 does not interfere with the operation of the medical device 100 (e.g., extension of the needles 150 from the apertures 160).

In one example, the needles 150 may be extended between about 1.5 mm and about 14 mm, typically between about 5 mm and about 11 mm beyond the outer circumferential surface of the elongate cannula 120 to inject a therapeutic agent into the wall of the body lumen. In other examples, the needles 150 may be extended any other length suitable to inject a therapeutic agent a determined depth into a desired location within a patient's anatomy. In one example, the spine 229 (e.g., the outer edge or apex) of the projection 228 of the dilation cap 200 may be positioned between about 1 mm and about 9 mm, typically between about 2 mm and about 6 mm from the outer circumferential surface of the elongate cannula 120 to dilate the body lumen. In other examples, the spine 229 may be positioned at any other length from the outer circumferential surface of the elongate cannula 120 suitable to dilate a desired location within a patient's anatomy. Additionally, or alternatively, the needles 150 may extend farther beyond the outer circumferential surface of the elongate cannula 120 than the projection 228 by a distance of between about 1 mm and about 8 mm, typically between about 3 mm and about 5 mm.

To couple the dilation cap 200 to the medical device 100, the distal terminus 123 of the elongate cannula 120 of the medical device may be inserted into the cavity of the distal tip 210 of the dilation cap as shown in FIG. 7. With the distal terminus 123 of the medical device 100 positioned within the cavity of the distal tip 210 of the dilation cap 200, the proximal coupling member 230 may be snapped or clipped onto the elongate cannula 120. To that end, the proximal coupling member 230 of the dilation cap 200 may be pushed toward the elongate cannula 120 of the medical device 100. The force of the elongate cannula 120 against the free ends 233, 235 of the first and second arms 232, 234 of the proximal coupling member 230 may cause the first and second arms to move away from one another toward the expanded configuration as described above. The aperture 236 between the free ends 233, 235 of the first and second arms 232, 234 may be sufficiently enlarged that the elongate cannula 120 may pass through the aperture 236 and into the opening formed between the first and second arms. The first and second arms 232, 234 may move toward the contracted configuration to engage (e.g., to squeeze) the elongate cannula 120 between the first and second arms.

The dilation cap 200 may be coupled to a medical device as described above with reference to the medical device 100. In one example, the dilation cap 200 may be removably coupled to the medical device. This may enable the medical device to be used with or without the dilation cap 200 attached to the medical device. In other words, a physician may determine whether to use the medical device with or without the dilation cap 200. Such a determination may be based on factors such as the size of the body lumen into which the medical device is to be introduced, physician preference, or any other factor. For example, a physician may choose to use the dilation cap 200 to perform a procedure involving an atypically large body lumen. Additionally, or alternatively, the dilation cap 200 may be configured to be coupled to an existing medical device. In other words, the dilation cap 200 may be configured to be coupled to an elongate cannula of a medical device without modification of the structure or configuration of the medical device. In this manner, the dilation cap 200 may be used with a medical device (e.g., an existing medical device) without requiring substantial design changes to the medical device.

Figure 9:
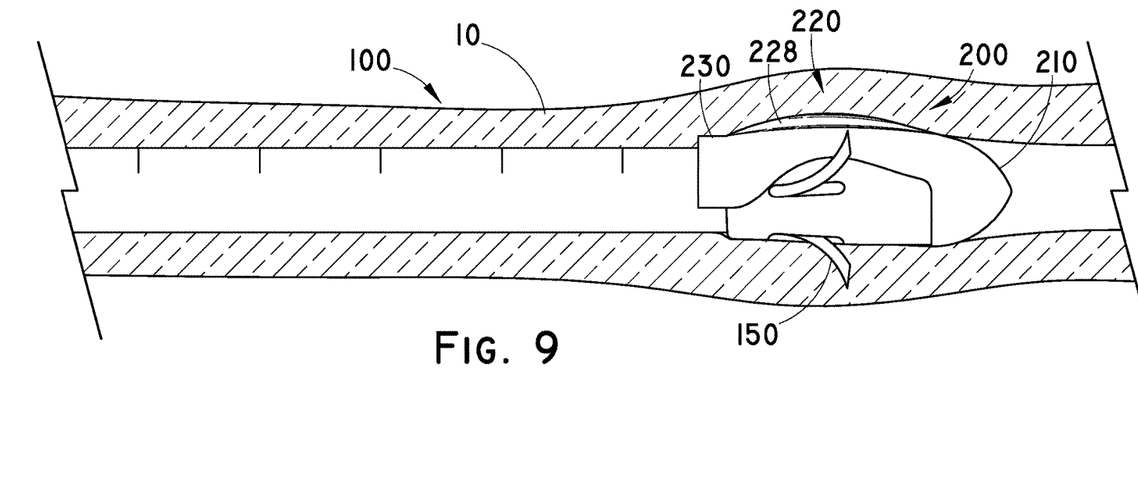
FIG. 9 illustrates a dilation cap removably coupled to a medical device as shown in FIGS. 7-8 and introduced into a body lumen.

FIG. 9 shows the dilation cap 200 coupled to the medical device 100 and introduced into a body lumen. Although FIG. 9 is described with reference to the dilation cap 200 shown in FIGS. 4-6, the description is equally applicable to the dilation cap 300 shown in FIGS. 10-12. The medical device 100 may be introduced into the body lumen with the needles 150 disposed within the lumen of the elongate cannula 120 as described above. The medical device 100 may be advanced within the body lumen until the distal portion 122 reaches a desired site for injection of a therapeutic agent. Once in position within the body lumen, the needles 150 of the medical device 100 may be extended out through the apertures 160 as described above. Upon extension of the needles 150, the needles may penetrate or pierce a wall 10 of the body lumen. One or more therapeutic agents may be introduced into the wall 10 via the needles 150.

Upon introduction of the medical device 100 within the body lumen, the projection 228 of the dilation cap 200 may engage a circumferential segment of the wall 10 of the body lumen. For example, the projection 228 may engage a circumferential segment of the wall 10 of the body lumen corresponding to the 12 o'clock position Z (see FIG. 8) as shown in FIG. 9. The offset configuration of the projection 228 may cause the distal portion 122 of the medical device 100 to be positioned near a circumferential segment of the wall 10 opposite the circumferential segment engaged by the projection 228. In other words, the offset configuration of the projection 228 may cause the distal portion 122 of the medical device 100 to be pushed toward a circumferential segment of the wall positioned opposite the circumferential segment engaged by the projection. In one example, the dilation cap 200 may be configured such that the second aperture 160b of the medical device (corresponding to the 6 o'clock position X) may be pushed into contact with the wall 10 of the body vessel as shown in FIG. 9. This may provide unidirectional support (e.g., at the 12 o'clock position) for the distal portion 122 of the medical device 100 during deployment of the needles 150.

Additionally, or alternatively, the projection 228 of the dilation cap 200 may be configured to dilate (e.g., tension, stretch, or tighten) the wall 10 of the body vessel. Such dilation of the wall 10 may facilitate penetration of the needles 150 into the wall. For example, in the absence of the dilation provided by the projection 228 of the dilation cap 200, the wall 10 of the body vessel may have a tendency to tent or move outward away from the distal portion 122 of the medical device 100 upon extension of the needles 150 to penetrate the wall of the body vessel. By dilating the wall 10 of the body vessel, the projection 228 may reduce such tenting of the wall upon extension of the needles 150. For example, such dilation may at least partially balance or distribute the forces applied to the wall 10 of the body vessel (e.g., by the needles 150 and the dilation cap 200) during extension of the needles 150. Such reduced tenting may enable the needles 150 to penetrate the wall 10 of the body vessel more consistently and/or smoothly, which may facilitate an injection procedure. In one example, the force that must be applied to the needles 150 to penetrate the wall 10 of the body vessel may be reduced relative to use of the medical device without the dilation cap. Additionally, or alternatively, such reduced tenting may enable the needles 150 to penetrate the wall 10 of the body vessel at precise locations so that a therapeutic agent may be injected as desired by the physician. In other words, the dilation cap 200 may enable consistent, controlled penetration of the needles 150 (or other piercing or cutting device) through the wall 10 of the body vessel.

Figure 10:
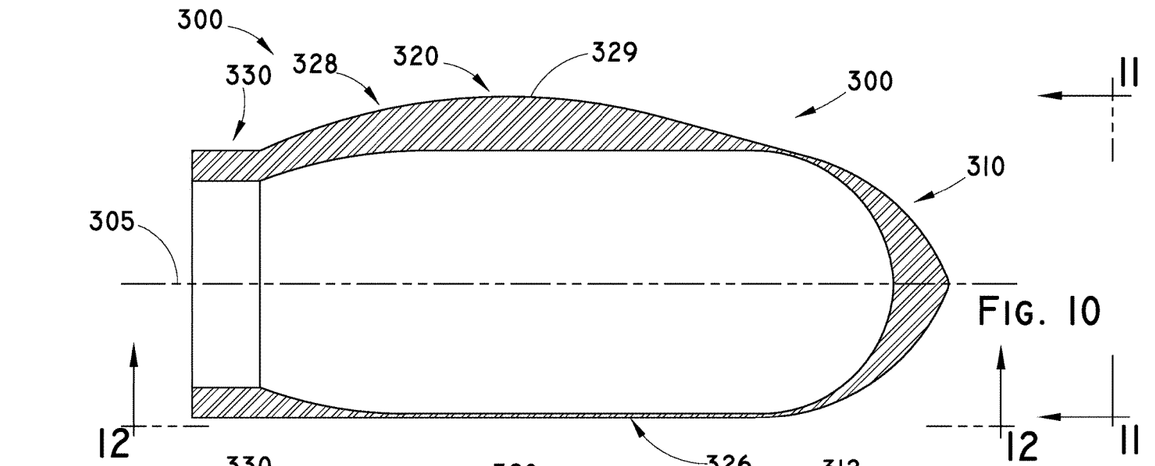
FIG. 10 is a side view of another example of a dilation cap configured to be coupled to a medical device.
Figure 11:
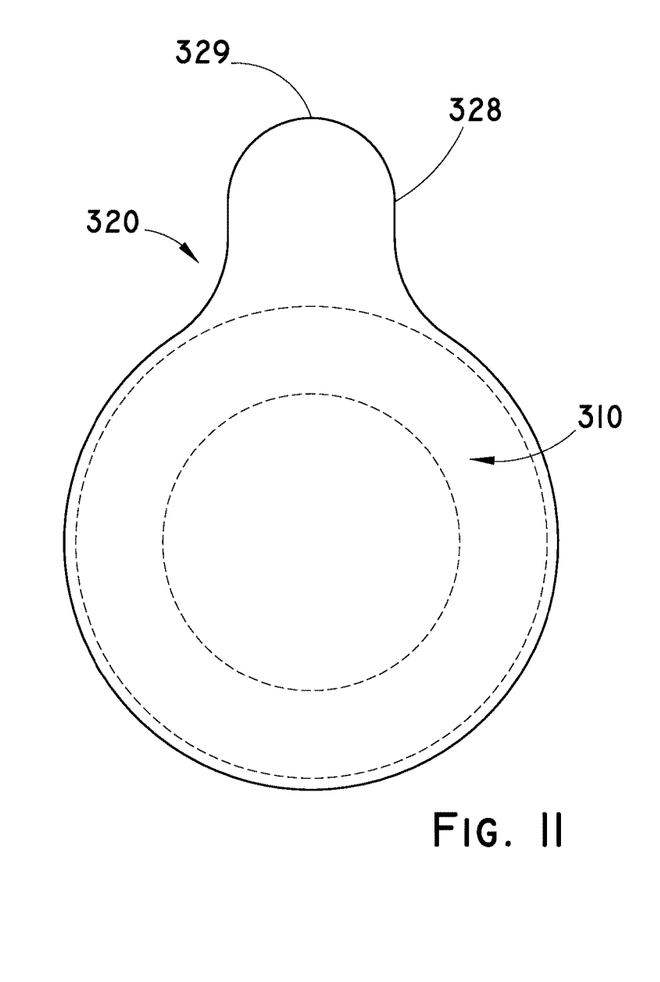
FIG. 11 is a front view of the dilation cap of FIG. 10.
Figure 12:
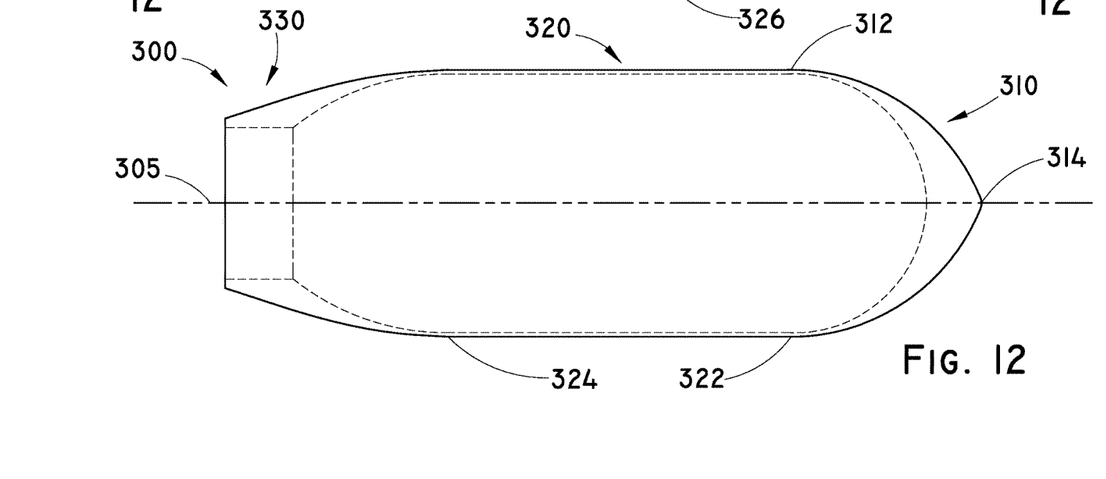
FIG. 12 is a bottom view of the dilation cap of FIGS. 10-11.

FIGS. 10-12 illustrate another embodiment of a dilation cap 300, which may be coupled to a medical device. The dilation cap 300 may be similar in some aspects to the dilation cap 200 described above. For example, the dilation cap 300 may include a distal tip 310, an intermediate body 320, and a proximal coupling member 330. The distal tip 310 may at least partially surround the longitudinal axis 305 of the dilation cap 300 to form a cavity within the distal tip. The cavity may be configured to receive an elongate cannula of a medical device as described above. A proximal end 314 of the distal tip 310 may be configured as a band or ring surrounding the longitudinal axis 305 of the dilation cap 300. The proximal end 314 may be an open end in communication with the cavity of the distal tip 310. A distal end 312 of the distal tip 310 may be a closed end. The distal tip 310 may be configured as an atraumatic tip or contoured nose as described above with reference to the distal tip 210 of the dilation cap 200.

The intermediate body 320 may extend proximally from the distal tip 310. The intermediate body 320 may have a distal end 322, which may be attached to the distal tip 310, and a proximal end 324, which may be attached to the proximal coupling member 330. In one example, the intermediate body 320 may include a tubular member 326 as best shown in FIG. 10. The tubular member 326 may extend longitudinally between the distal tip 310 and the proximal coupling member 330. The tubular member 326 may surround the longitudinal axis 305 of the dilation cap 300 to define a lumen extending longitudinally within the tubular member. The tubular member may be coaxial with the dilation cap. In one example, the tubular member 326 of the intermediate body 320 may be substantially cylindrical. In other examples, the tubular member 326 may have any other tubular shape. In one example, the intermediate body 320 may include one or more apertures (not shown), which may be configured to align with the apertures 160 and/or the needles 150 of the medical device 100. In other examples, the intermediate body 320 may include any number of apertures configured to align with any type of aperture, needle, or cutting device of a medical device.

The intermediate body 320 may include a dilator portion, which may include a contoured outer surface as described above with reference to the dilation cap 200. In one example, the dilator portion may include a projection 328 extending laterally in a direction away from the longitudinal axis 305 of the dilation cap 300. The projection 328 may be configured as a dilation keel extending longitudinally along the intermediate body 320 and laterally away from the longitudinal axis 305 of the dilation cap 300 as shown in FIGS. 10-11. The projection 328 may include a rounded outer edge positioned opposite an inner edge, which may be attached to the tubular member 326. The projection 328 may include a spine 329, which may define the outermost edge of the intermediate body 320 and/or the dilation cap 300. The projection 328 may include a tapered distal end and/or a tapered proximal end. In one example, both the proximal end and the distal end of the projection 328 may be tapered as shown in FIG. 10. This may aid in advancing and/or retracting the dilation cap 300 within a body lumen.

The projection 328 may be configured such that a cross section of the dilator portion of the intermediate body 320 has an eccentric shape with respect to the longitudinal axis 305 of the dilation cap 300. In other words, the projection 328 may be offset with respect to the longitudinal axis 305 of the dilation cap 300 such that the intermediate body 320 is not symmetrical about the longitudinal axis. In this manner, the dilation cap 300 may impose a greater outward force on a circumferential segment of a body lumen aligned with the projection 328 than on another circumferential segment of the body lumen misaligned with the projection 328 as described above.

The proximal coupling member 330 may extend proximally from the intermediate body 320. The proximal coupling member 330 may include a tubular member surrounding the longitudinal axis 305 of the dilation cap 300 and defining a lumen extending longitudinally within the proximal coupling member. The tubular member of the proximal coupling member 330 may be integral with or separate from the tubular member 326 of the intermediate body 320. The dilation cap 300 may be configured such that the cavity of the distal tip 310, the lumen of the intermediate body 320, and the lumen of the proximal coupling member 330 may cooperatively define a continuous pathway within the dilation cap. In one example, at least a portion of the projection 228 of the intermediate body 220 may extend longitudinally along (e.g., overlap with) the proximal coupling member 330. Additionally, or alternatively, the proximal coupling member 330 may include a tapered outer surface. For example, the outside diameter of the cross section of the proximal coupling member 330 may decrease longitudinally in a proximal direction as shown in FIGS. 10 and 12. This may aid in advancing and/or retracting the dilation cap 300 within a body lumen.

The proximal coupling member 330 may be configured to engage an intermediate portion of an elongate cannula of a medical device. In one example, the proximal coupling member 330 may be configured as a sleeve (e.g., a band or a ring) configured to receive the elongate cannula of the medical device. The proximal coupling member 330 may be movable between a contracted configuration and an expanded configuration. To that end, the proximal coupling member 330 may be formed from an elastomeric material such as, for example, silicone. In the contracted configuration, the lumen of the proximal coupling member 330 may have a contracted diameter. In the expanded configuration, the lumen of the proximal coupling member 330 may have an expanded diameter that is larger than the contracted diameter. The proximal coupling member 330 may be biased toward the contracted configuration. The proximal coupling member 330 may be movable between the contracted configuration and the expanded configuration to engage a medical device as further described below.

The dilation cap 300 may be formed from any suitable material as further described below. In one example, the dilation cap 300 may be formed from silicone. Additionally, or alternatively, at least a portion of the dilation cap 300 (e.g., the projection 328) may be substantially non-expandable.

The dilation cap 300 may be coupled to any suitable medical device (e.g., the medical device 100). To couple the dilation cap 300 to the medical device 100, the distal portion 122 of the elongate cannula 120 of the medical device may be introduced into the lumen of the proximal coupling member 330. In the contracted configuration, the lumen of the proximal coupling member 330 may have a diameter that is smaller than the diameter of the distal portion 122 of the elongate cannula 120 of the medical device 100. Upon introduction of the distal portion 122 of the elongate cannula 120 into the proximal coupling member 330, the proximal coupling member may expand toward the expanded configuration to receive the elongate cannula. The elongate cannula 120 may be advanced distally within the pathway defined by the lumen of the proximal coupling member 330, the lumen of the intermediate body 320, and the cavity of the distal tip 310 until the distal terminus 123 of the medical device 100 is received within the cavity of the distal tip 310 of the dilation cap 300. The proximal coupling member 330, the intermediate body 320, and/or the distal tip 310 may engage the outer surface of the elongate cannula 120 to retain the dilation cap 300 in place relative to the elongate cannula.

In any of the examples described herein, the dilation cap may be formed from any suitable material. For example, the dilation cap may be formed from silicone, vinyl, latex, acrylonitrile butadiene styrene (ABS), polyurethane, polyether ether ketone (PEEK), polyethylene terephthalate (PET), polyethylene oxide (PEO), polystyrene, polyamide, polyvinyl chloride (PVC), polytetrafluoroethylene (PTFE), expanded polytetrafluoroethylene (ePTFE), pyrolytic carbon, a cobalt-chromium alloy (e.g., cobalt-chrome), nitinol, stainless steel, or any polymeric or non-polymeric material. The various components of the dilation cap (e.g., the distal tip, the intermediate body, and/or the proximal coupling member) may be formed separately or integrally with one another. In one example, the dilation cap may be formed by a molding process such as injection molding.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system configured to be introduced into a body lumen of a patient, the system comprising:
    a medical device comprising an elongate cannula extending along a longitudinal axis and having a distal end and an intermediate portion positioned proximal of the distal end; and
    a dilation cap removably coupled to the elongate cannula of the medical device, wherein the dilation cap comprises a cavity, the distal end of the elongate cannula received within the cavity, the dilation cap further comprising:
        a distal tip;
        an intermediate body extending proximally from the distal tip and comprising a dilator portion and an opening exposing the cavity, the dilator portion comprising a projection extending laterally in a direction away from the longitudinal axis of the elongate cannula, wherein the projection is longitudinally aligned with the opening and is circumferentially offset from the opening, and wherein when the dilation cap is coupled to the elongate cannula, an inner surface of the intermediate body engages an outer surface of the distal end of the elongate cannula, and a circumferential portion of the outer surface of the elongate cannula is aligned longitudinally with the opening of the intermediate body of the dilation cap; and
        a proximal coupling member extending proximally from the intermediate body and at least partially surrounding the intermediate portion of the elongate cannula to retain the dilation cap in place relative to the elongate cannula.

2. The system of claim 1, wherein the elongate cannula of the medical device comprises an outer circumferential surface defining a plurality of circumferential segments positioned around the outer circumferential surface, and the projection of the dilation cap is circumferentially aligned with one of the plurality of circumferential segments.

3. The system of claim 2, wherein the medical device comprises a plurality of apertures, each of the plurality of apertures is disposed on the outer circumferential surface of the elongate cannula, and one of the plurality of apertures is disposed on each circumferential segment with the exception of the circumferential segment with which the projection of the dilation cap is circumferentially aligned.

4. The system of claim 3, wherein when the dilation cap is posited upon the distal end of the elongate cannula, the plurality of apertures are each exposed through the dilation cap.

5. The system of claim 2, wherein the plurality of circumferential segments comprises a first quadrant, a second quadrant, a third quadrant, and a fourth quadrant, the elongate cannula of the medical device comprises a plurality of apertures, each of the plurality of apertures is disposed on the outer circumferential surface of the elongate cannula and in fluid communication with a lumen extending longitudinally within the elongate cannula, a first of the plurality of apertures is disposed on the first quadrant, a second of the plurality of apertures is disposed on the second quadrant, a third of the plurality of apertures is disposed on the third quadrant, and the projection of the dilation cap is circumferentially aligned with the fourth quadrant.

6. The system of claim 5, wherein when the dilation cap is positioned upon the distal end of the elongate cannula, each of the first, second, and third plurality of apertures are exposed through the dilation cap.

7. The system of claim 1, wherein an outer surface of the dilator portion of the intermediate body is asymmetrical with respect to the longitudinal axis of the medical device.

8. The system of claim 1, wherein the intermediate body comprises a rib extending longitudinally between the distal tip and the proximal coupling member and adjacent to the elongate cannula of the medical device.

9. The system of claim 1, wherein the intermediate body comprises a tubular sleeve surrounding a circumferential portion of the elongate cannula of the medical device.

10. The system of claim 1, wherein the projection comprises a dilation keel extending longitudinally along the intermediate body and laterally away from the longitudinal axis of the dilation cap.

11. The system of claim 10, wherein the dilation keel comprises a spine extending along an outer edge of the dilation keel, and a distance between the spine and the longitudinal axis of the dilation cap increases from a distal end of the dilation keel to an intermediate point of the dilation keel in a proximal direction.

* * * * *